(12) United States Patent
Rathjen (10) Patent No.: US 8,480,231 B2
(45) Date of Patent: *Jul. 9, 2013

(54) OPHTHALMOLOGICAL MEASURING DEVICE AND MEASUREMENT METHOD

(75) Inventor: Christian Rathjen, Bremen (DE)

(73) Assignee: SIS AG, Surgical Instrument Systems (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/113,586

(22) Filed: May 23, 2011

(65) Prior Publication Data

US 2011/0222021 A1 Sep. 15, 2011

Related U.S. Application Data

(63) Continuation of application No. 12/850,175, filed on Aug. 4, 2010, now Pat. No. 8,025,401.

(60) Provisional application No. 61/231,459, filed on Aug. 5, 2009.

(51) Int. Cl.
*A61B 3/10* (2006.01)
*A61B 3/14* (2006.01)
*A61B 3/00* (2006.01)

(52) U.S. Cl.
USPC ............ 351/205; 351/210; 351/221; 351/246

(58) Field of Classification Search
USPC ................... 351/200, 205–206, 210, 221, 246
See application file for complete search history.

(56) References Cited

U.S. PATENT DOCUMENTS

| | | | |
|---|---|---|---|
| 2002/0036750 A1* | 3/2002 | Eberl et al. | 351/207 |
| 2002/0171804 A1* | 11/2002 | Rathjen | 351/221 |
| 2003/0160943 A1* | 8/2003 | Xie et al. | 351/209 |
| 2004/0036838 A1* | 2/2004 | Podoleanu et al. | 351/206 |
| 2005/0024586 A1* | 2/2005 | Teiwes et al. | 351/209 |
| 2007/0273611 A1* | 11/2007 | Torch | 345/8 |
| 2008/0219515 A1* | 9/2008 | Namgoong | 382/117 |

\* cited by examiner

Primary Examiner — Dawayne A Pinkney
(74) Attorney, Agent, or Firm — Ostrolenk Faber LLP (57) ABSTRACT

An ophthalmological measuring device for determining geometric structures in an eye includes an optical, triangulating measurement system for determining at least one geometric reference in the eye by triangulation, and an optical, interferometric measurement system for determining geometric detailed structures in the eye by optical interferometry. The measuring device is designed to position the geometric detailed structures determined by the interferometric measurement system on the basis of the at least one geometric reference in the eye determined by the triangulating measurement system. This firstly allows the interferometric measurement system to register geometric detailed structures in the eye with a high optical resolution and at places that are not visible to the triangulating measurement system, and secondly allows the positioning of said geometric detailed structures in the eye on the basis of geometric references that are determined by the triangulating measurement system without significant movement artifacts.

18 Claims, 6 Drawing Sheets

OPHTHALMOLOGICAL MEASURING DEVICE AND MEASUREMENT METHOD

CROSS REFERENCE TO RELATED APPLICATIONS

The present application is a continuation application of U.S. patent application Ser. No. 12/850,175 filed Aug. 4, 2010 entitled OPHTHALMOLOGICAL MEASURING DEVICE AND MEASUREMENT METHOD which claims benefit of and priority to U.S. Provisional Patent Application Ser. No. 61/231,459 filed Aug. 5, 2009 entitled OPHTHALMOLOGICAL MEASURING DEVICE AND MEASUREMENT METHOD, the entire contents of which are hereby incorporated by reference herein.

BACKGROUND

1. Field of the Disclosure

The present disclosure relates to an ophthalmological measuring device and an ophthalmological measurement method for determining geometric structures of an eye. In particular, the present invention relates to an ophthalmological measuring device and an ophthalmological measurement method for determining geometric structures of an eye, in which use is made of an optical, triangulating first measurement system and an optical, interferometric second measurement system.

2. Related Art

The laid-open specification DE 10 2007 017 599 describes an ophthalmological measurement system and an ophthalmological measurement method for determining geometric parameters in the front eye section, which parameters are required for calculating the refraction of intraocular lenses. The measurement system according to DE 10 2007 017 599 comprises, combined in a single instrument, a first measuring device for determining the axial length and a second measuring device for registering a plurality of structures in the front section such as the cornea, anterior chamber and lens. Here, the first measuring device comprises a known optical coherence interferometer (PCI=partial coherence interferometry, OCT=optical coherence tomography) operating in the time or frequency domain. The second measuring device comprises a slit illumination unit and an imaging unit for carrying out a known slice-image method. The measurement system moreover comprises a control unit designed to evaluate both the measured values required to measure the axial length and the angular and distance conditions required for a triangulation on the eye, with sections, radii and/or angles of refraction being determined from the slice images of the front eye sections supplied by the imaging unit.

The advantage of triangulating measuring devices with a slice-image method compared to those based on one or more individual beams is that triangulating slice-image methods do not generate any, or only generate few, movement artifacts caused by eye movements and thus have a comparatively higher geometric precision with the same number of measurement points. Furthermore, in the Scheimpflug configuration there is the additional advantage of allowing the depth measurement range at high optical resolution to be designed to be significantly greater than in interferometric methods. This holds true for both the lateral resolution and the depth resolution. In triangulation methods and in interferometric methods with a single scanned beam, the movement artifacts caused by eye movements generate measurement errors, which have to be corrected by an additional method that registers the eye movements. In order to be effective, such a method, not known previously, would have to be significantly faster and more precise than the measurement errors caused by the eye movements. In turn, triangulation methods with many individual beams or with structured illumination are disadvantageous in that the number of measurement points is limited and, moreover, the depth measurement range is severely limited because the imaging unit cannot be arranged in Scheimpflug configuration for all beams. The known triangulating measuring devices generally are disadvantageous in that the measurement region thereof that can be registered is limited to the front eye region (anterior chamber region), which can be illuminated directly, and the posterior chamber of the eye is not visible. In the process, the measurement region of the known triangulating measuring devices is further limited by opacity, e.g. in the cornea, by implants, e.g. lenses placed in front, and by the iris, and certain partial regions, such as the anterior chamber angle, cannot, in general terms, be registered by the known triangulating measuring devices due to tissue properties.

The advantage of known optical coherence interferometers is that the measurement region thereof that can be registered is not limited to the front eye region (anterior-chamber region) because the posterior chamber of the eye can also be measured due to the axial operating principle of these interferometers. In conventional interferometric methods, use is typically made of a scanning beam. In the process, the beam at a particular position generates a depth scan (A-scan) at this location. Relative displacement of measurement object and light beam, or scanning the beam, extends the depth scan over a contiguous surface along a scan line (B-scan). A three-dimensional scan (C-scan) is assembled from a plurality of B-scans. Thus, as soon as the interferometric methods are used for the structural measurement at a plurality of positions, eye movements generate movement artifacts and hence measurement errors. Moreover, compared to triangulating measurement methods in Scheimpflug configuration, there is the additional disadvantage that the depth measurement range of interferometric methods has to be designed to be significantly smaller at a high lateral resolution. Since the focal depth region decreases disproportionately with image resolution for optical reasons, the desire for high lateral resolution generally significantly restricts the depth measurement range, particularly in interferometric methods.

At this juncture, reference is additionally made to the fact that there are further interferometric (OCT-) methods, which can simultaneously register a plurality of A-scans (with a plurality of light beams) by means of optical parallelization. Furthermore, there are en-face techniques, which successively scan a plurality of planes at depth in order to subsequently synthesize A- and B-scans. Some of these techniques can be used to reduce movement artifacts. However, disadvantages of these techniques include the high technical and financial expenditure required for this, a reduced resolution and/or compromises (limitations) in the depth measurement range. It can be observed that there are no commercially available systems with movement- and artifact-free interferometric methods. [Drexler] provides a good overview of the prior art.

Even if triangulating methods and interferometric (OCT-) methods can be used for the geometric measurement technique, it should be noted here that they are based on different effective principles. While the operational principle of triangulating methods is based on diffuse scattering in the tissue and on surfaces in a large spatial area, interferometric methods operate with backward reflection in respect of the projecting optical system. Hence both methods supply different items of information, and thus overall more information, relating to the structural properties of the measurement object in addition to the geometry thereof.

SUMMARY

It is an object of the present invention to propose an ophthalmological measuring device and an ophthalmological measurement method for determining geometric structures of an eye, which do not have at least some of the disadvantages of the known systems. More particularly, it is an object of the present invention to propose an ophthalmological measuring device and an ophthalmological measurement method for determining geometric structures of an eye, which, on the one hand, are not limited to the visible measurement region of known triangulating measurement methods and, on the other hand, have a reduced impairment of the measurement accuracy by movement artifacts compared to known interferometric methods.

According to the present invention, these objects are achieved in particular by the elements of the independent claims. Additional advantageous embodiments moreover emerge from the dependent claims and the description.

More particularly, the aforementioned objects are achieved by the present invention by virtue of the fact that an ophthalmological measuring device for determining geometric structures of an eye, more particularly geometric structures in the region of the anterior chamber of the eye, includes an optical, triangulating first measurement system for determining at least one geometric reference in the eye by triangulation and an optical, interferometric second measurement system for determining (two- and/or three-dimensional) geometric detailed structures in the eye (particularly in the region of the anterior chamber of the eye) by optical interferometry, and by virtue of the fact that the measuring device is configured to register and store the geometric detailed structures determined by the second measurement system, and to position the geometric detailed structures, registered and stored by the measuring device, on the basis of the at least one geometric reference in the eye determined by the first measurement system. Since triangulating measurement systems, more particularly light-slit-(light-section-) based measurement systems, generate no or only insubstantial movement artifacts (for example, 30 to 60 light-slit recordings suffice for an overall topology of the cornea in triangulating measurement systems, whereas more than 500 axial measurements on 30 to 60 scan surfaces are needed for this in interferometric measurement), and since interferometric measurement systems can be designed for a detailed measurement region that is smaller compared to the measurement region of the triangulating measurement system but has a high optical resolution, the positioning of the geometric detailed structures in the eye on the basis of the geometric reference allows a particularly advantageous combination of triangulating and interferometric measurement methods. On the one hand, geometric detailed structures can be registered in the eye by the interferometric measurement system with a high optical resolution and at positions that are not visible to the triangulating measurement system, and, on the other hand, they can be positioned in the eye on the basis of geometric references, which are determined by the triangulating measurement system without significant movement artifacts. Hence, the advantages of the interferometric measurement system are combined with the advantages of the triangulating measurement system. The reduced impairment in respect of movement artifacts additionally allows the use of cost-effective, slower interferometric (OCT-) techniques (in particular time-domain OCT), which advantageously have greater depth measurement ranges and also allow the use of other wavelengths (in particular wavelengths>1000 nm).

In one embodiment variant, the first measurement system and the second measurement system are mechanically coupled such that the geometric detailed structures in the eye can be positioned on the basis of one or more geometric settings in a position of the first measurement system (11) corresponding to the geometric reference. In other words, the triangulating measurement system and the interferometric measurement system are set up in a mechanical/geometric fashion, preferably by means of a calibration body, for registering one or more defined geometric references of the eye and the geometric settings are determined from this defined geometric calibration position, which settings define a calibrated relationship between the triangulating measurement system and the interferometric measurement system and, in a defined position of the triangulating measurement system (with respect to the eye), allow a positioning of the geometric detailed structures determined by the interferometric measurement system. An advantage of this variant is that there is no need for an image registration and assignment of geometric structure features and positioning of the geometric detailed structures on the basis thereof if the geometric detailed structures are registered by the interferometric measurement system in prompt fashion (i.e. within a defined timeframe) with respect to the setting of the triangulating measurement system corresponding to the geometric reference.

In a further embodiment variant, the measuring device includes a positioning module designed to determine one or more geometric reference features of the eye and to position the geometric detailed structures on the basis of the geometric reference features in the eye. In other words, the geometric detailed structures are positioned in the eye on the basis of geometric reference features of the eye, which, on the one hand, are determined as a geometric reference by the triangulating measurement system and, on the other hand, are determined in the geometric detailed structures by the interferometric measurement system. An advantage of this variant is that a user does not need to undertake a mechanical/geometric set-up of the triangulating measurement system with respect to a defined geometric reference of the eye before the interferometric measurement system can register the geometric detailed structures as a result of this. That is to say the triangulating and the interferometric measurement methods can be carried out (temporally) independently of one another without bothersome influences of eye movements, that is to say both in parallel/simultaneously and sequentially and deferred.

The first measurement system preferably includes a light projector for projecting a light slit (light section) and a first scan module for moving the light slit to different positions of the eye, and the second measurement system includes an interferometer and a second scan module, with the second scan module being designed to project at least one light beam from the interferometer onto and into the eye at a plurality of different positions of the eye and to supply light reflected by the eye to the interferometer (interferometers operating in parallel use a plurality of light beams simultaneously).

In one variant, the triangulating first measurement system and the interferometric second measurement system have a common light source. More particularly, the interferometer supplies not only the light for the light beam, but also the light for the light slit (light section) of the triangulating measurement system.

In one embodiment variant, the first scan module is designed to move the light slit along a scan direction, and the second scan module is designed to move the light beam in a scan plane substantially parallel to or substantially normal to the scan direction. In the former case, the scanning by the interferometric measurement system is for example carried out perpendicularly to the light slit, in the latter case it is, for example, carried out in the light slit or parallel thereto. The light slit and the light beam are respectively moved by deflection by means of a deflection mirror or by displacing a corresponding projector or mirror by means of a movement driver.

In a further embodiment variant, the first scan module is designed to move the light slit by rotation about a rotational axis substantially running in the light slit, and the second scan module is designed to move the light beam in a scan plane, with a central projection axis of the second scan module forming an angle with the rotational axis or running along the rotational axis. Scanning the eye by rotating the light slit allows a particularly simple embodiment of the triangulating measurement system, without deflection mirrors or translational movement drivers.

In another embodiment variant, the first scan module and the second scan module are designed and coupled such that the light slit and the scan plane are situated in a common plane.

In a further embodiment variant, the light slit projected by the light projector and the light beam from the interferometer have different wavelengths. By way of example, the wavelength of the projected light slit is less than 500 nm and the wavelength of the light beam from the interferometer is more than 1000 nm, more particularly 1300 nm.

The first measurement system preferably includes at least one camera arranged in Scheimpflug configuration for registering cross-sectional parts of the eye illuminated by the light slit.

In a further embodiment variant, the measuring device includes a processing module designed to register a plurality of geometric detailed structures positioned differently in the eye, to position these geometric detailed structures with respect to one another on the basis of the at least one geometric reference and to assemble said structures to form a superordinate combined geometric detailed structure.

In one embodiment variant, the processing module is designed to deform suitably the geometric detailed structures for assembling the superordinate combined geometric detailed structure.

The first measurement system is preferably designed to determine the geometric reference in a defined reference measurement region of the eye, the second measurement system is designed to determine the geometric detailed structures in a detailed measurement region of the eye, which detailed measurement region is significantly smaller than the defined reference measurement region, and the measuring device includes movement drivers for moving the second measurement system for determining geometric detailed structures in a plurality of different detailed measurement regions of the eye.

In one embodiment variant, the detailed measurement region of the eye can be arranged within the defined reference measurement region, overlapping with the defined reference measurement region, adjoining the defined reference measurement region and/or outside of the defined reference measurement region.

Additionally, the present invention relates to an ophthalmological measurement method for determining geometric structures of an eye, which includes the following steps: determining at least one geometric reference in the eye by an optical, triangulating first measurement system, determining geometric detailed structures in the eye by an optical interferometric second measurement system, registering and storing the geometric detailed structures in the eye determined by the second measurement system, and positioning the geometric detailed structures, registered and stored, on the basis of the at least one geometric reference determined by the first measurement system.

BRIEF DESCRIPTION OF THE DRAWINGS

Hereinbelow, an embodiment of the present invention is described on the basis of an example. The exemplary embodiment is illustrated by the following attached figures.

DETAILED DESCRIPTION OF THE EMBODIMENTS

In FIGS. 1 to 11, the same reference signs denote functionally equivalent components, parts and systems; however, the specific embodiments of these functionally equivalent components, parts and system can vary in different embodiment variants.

Figure 1:
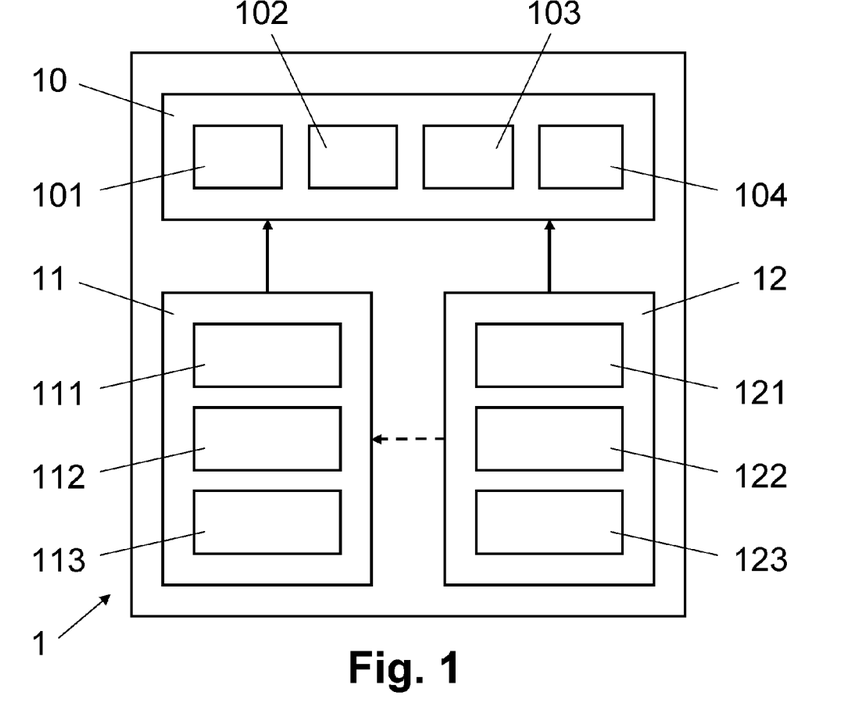
FIG. 1 shows a block diagram that schematically illustrates an ophthalmological measuring device comprising a triangulating measurement system, an interferometric measurement system and processing means.
Figure 2:
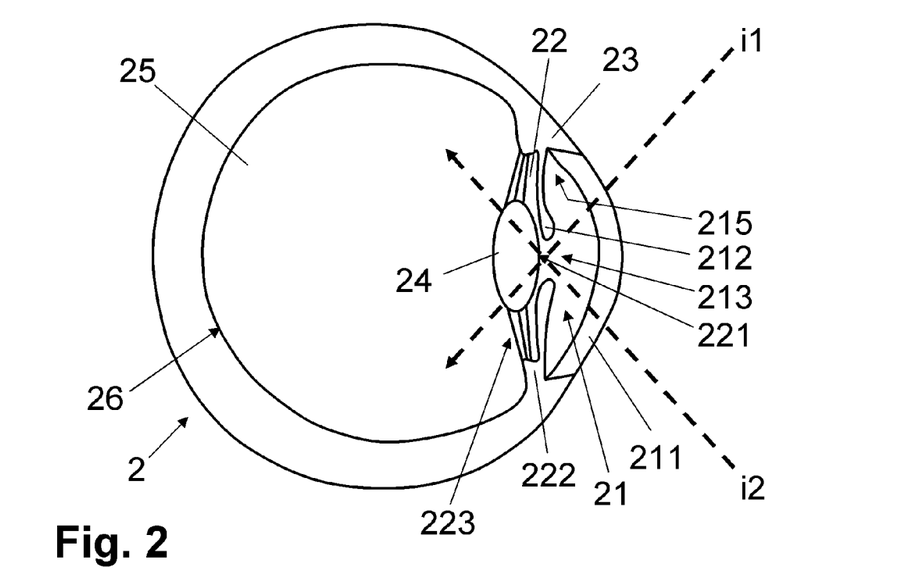
FIG. 2 shows a cross section through an eye with different geometric structures.

FIG. 1 illustrates an ophthalmological measuring device 1 for determining geometric structures of an eye 2. It can be gathered from FIG. 2 that these geometric structures comprise, for example, partial structures or complete structures in the anterior chamber region 21, such as the cornea 211, iris 212 and pupil 213, or anterior chamber angle 215, in the posterior chamber region 22 (or adjacent thereto), such as the front side 221 of the lens, ciliary bodies 222 or zonular fibers 223, in the region around the chamber of the eye, such as Schlemm's canal 23, and in the region behind the eye chamber, such as lens 24, vitreous humor 25 or retina 26, as well as inclusions and implants, more particularly transparent implants, in the anterior 21 or posterior 22 chamber region.

The measuring device 1 includes an optical, triangulating measurement system 11 for determining at least one (two- or three-dimensional) geometric reference in the eye 2 by triangulation, an optical, interferometric measurement system 12 for determining (two- or three-dimensional) geometric detailed structures in the eye 2 by optical interferometry, and processing means 10 for positioning in the eye 2 the geometric detailed structures determined by the interferometric measurement system 12 on the basis of the at least one geometric reference in the eye 2 determined by the triangulating measurement system 11.

Figure 3A:
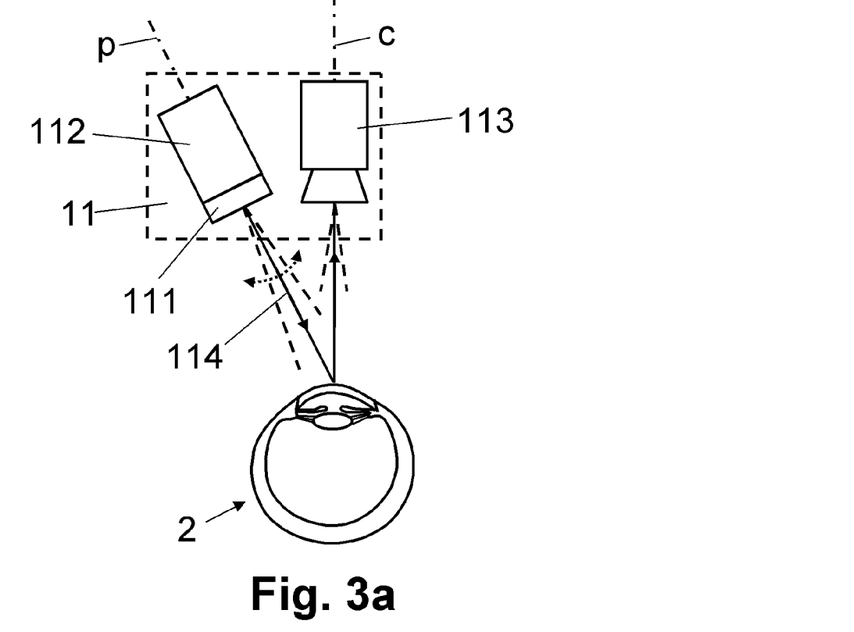
FIG. 3a shows a block diagram that schematically illustrates a triangulating measurement system comprising a light projector and a camera.
Figure 3B:
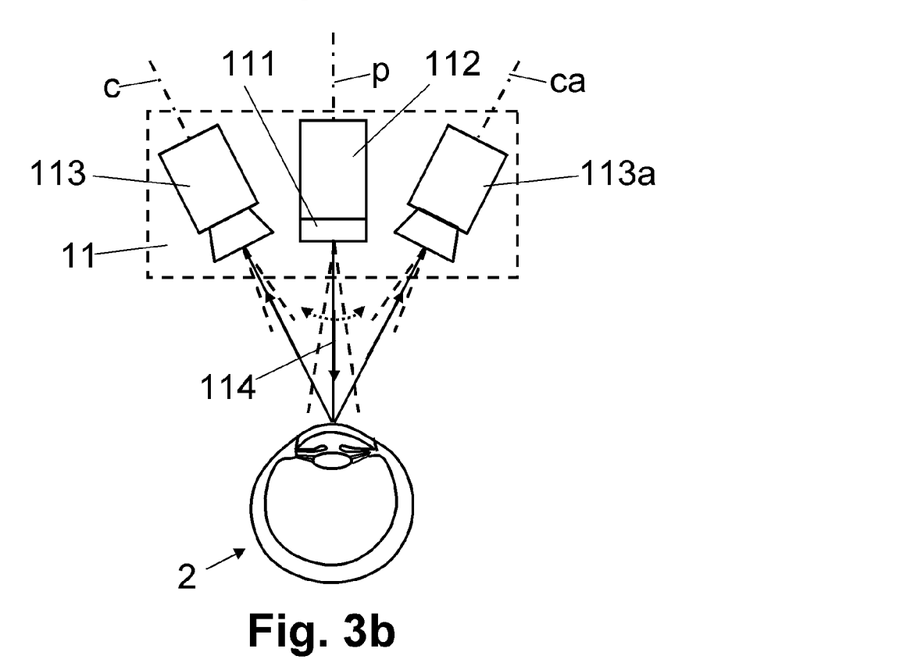
FIG. 3b shows a block diagram that schematically illustrates a triangulating measurement system comprising a light projector and two cameras.
Figure 4:
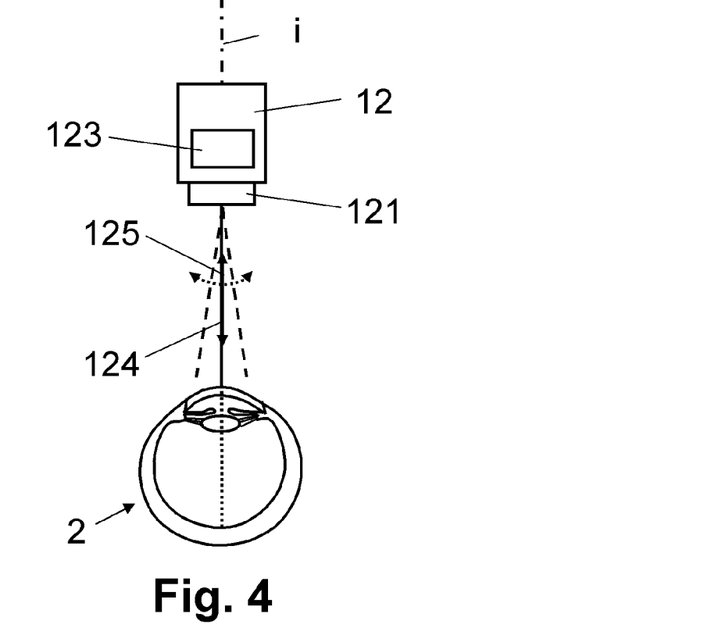
FIG. 4 shows a block diagram that schematically illustrates an interferometric measurement system comprising an interferometer and a scanner.
Figure 5:
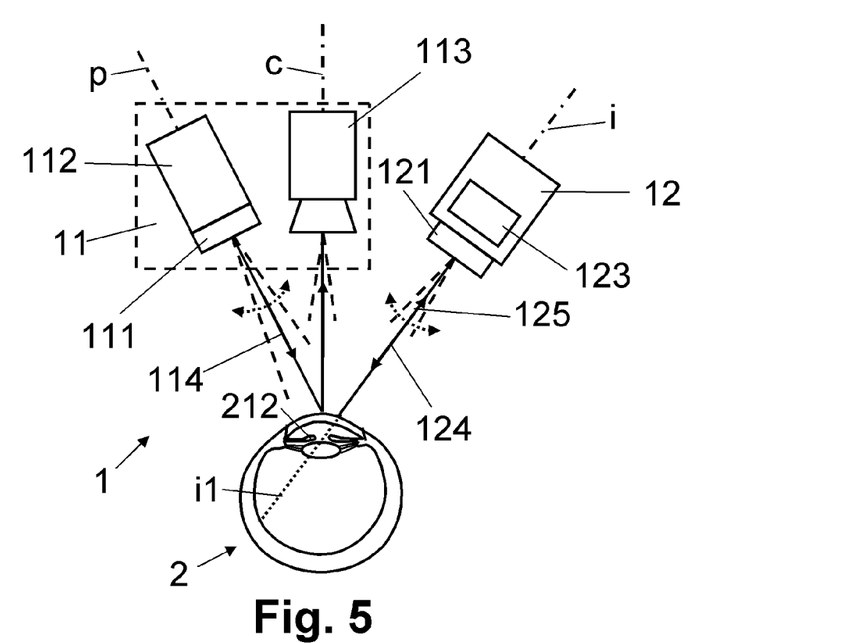
FIG. 5 shows a block diagram that schematically illustrates an arrangement of a triangulating measurement system and an interferometric measurement system of the ophthalmological measuring device.
Figure 6:
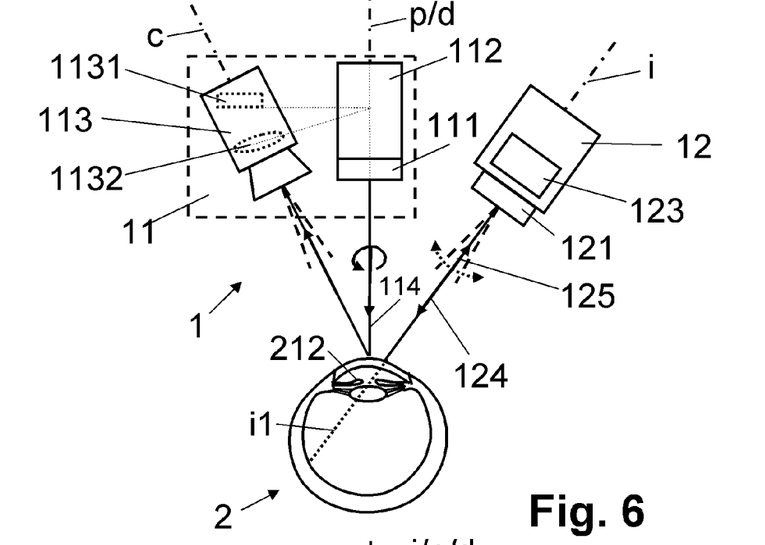
FIG. 6 shows a block diagram that schematically illustrates a rotatable arrangement of a triangulating measurement system and an interferometric measurement system of the ophthalmological measuring device.
Figure 7:
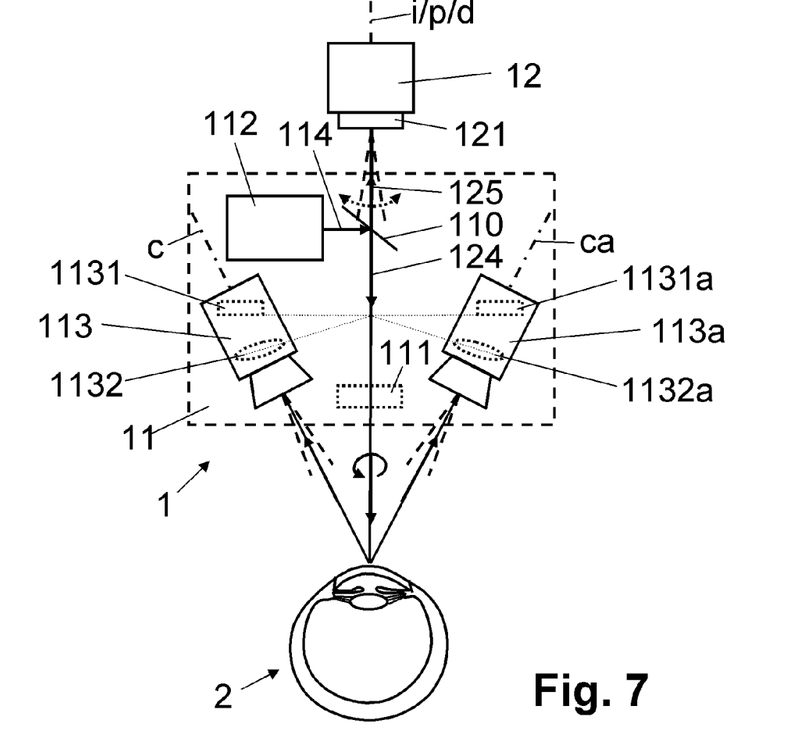
FIG. 7 shows a block diagram that schematically illustrates a further rotatable arrangement of a triangulating measurement system and an interferometric measurement system of the ophthalmological measuring device.

As illustrated schematically in FIGS. 1, 3a, 3b, 5, 6 and 7, the triangulating measurement system 11 includes a light projector 112 for projecting a light beam, preferably a light slit 114, and a scan module 111 for moving the light beam or the light slit 114 to different places in the eye 2, and also a camera 113, preferably arranged in Scheimpflug configuration, for registering diffuse reflections on the eye 2 generated by the light beam or cross-sectional parts of the eye 2 illuminated by the light slit 114. As illustrated in FIGS. 3a, 3b, 5, 6 and 7, the light projector 112 and the camera 113 are arranged in the triangulating measurement system 11 such that the projection axis p of the light projector 112 and the optical axis c of the camera—and correspondingly emitted or reflected light beams—form an angle. As a result, distance values— and hence the position and form—of two- and three-dimensional geometric structures can be determined as geometric references in the eye 2 by the processing means 10 as a result of evaluating triangular relationships (triangulation) on the basis of the reflections or illuminated cross-sectional parts registered by the camera 113. Hence, if a plurality of measurement beams are emitted simultaneously, more particularly during the preferred projection of a light slit 114, an instantaneous image of geometric structures in the eye 2 can be generated without bothersome movement artifacts. FIGS. 3b and 7 illustrate a particularly advantageous configuration of the triangulating measurement system 11 with two cameras 113, 113a arranged off the projection axis p and preferably arranged in Scheimpflug configuration, the optical axes c, ca of which cameras preferably being arranged mirror-symmetrically with respect to the projection axis p, which cameras are used to register from two recording perspectives the diffuse reflections on the eye 2 or the cross-sectional parts of the eye 2 illuminated by the light slit 114. Depending on the embodiment variant, the scanner 111 is designed to bring about the movement of the light beam or light slit 114 to different places in the eye 2 by deflecting a mirror and/or by translational or rotational mechanical movement of the light projector 112 by means of a movement driver. As indicated schematically in FIGS. 6 and 7, a scanner 111 with a rotational driver, more particularly in combination with a single or duplicate Scheimpflug camera as per FIG. 3b, is particularly preferred.

As illustrated schematically in FIGS. 1, 4, 5, 6 and 7, the interferometric measurement system 12 includes an interferometer 123 and a scan module 121 for projecting a light beam 124 from the interferometer 123 onto and into the eye 2 at a plurality of different positions in the eye 2, and for registering light reflected by the eye 2 and for supplying said light to the interferometer 123 (the projection optical system for the focused projection of the light beam 124 has not been illustrated). In one variant, the interferometer 123 and the scanner 121 are coupled for the bidirectional light transmission between the interferometer 123 and the scanner 121 via an optical transmission system 122, e.g. via an optical waveguide. In a further variant, the interferometer 123 is coupled via the optical transmission system 122 to the light projector 112 or scanner 111 of the triangulating measurement system 11 for supplying the light for the light slit 114 of the triangulating measurement system 11 from the light source of the interferometer 123.

In one embodiment variant, the light beam or light slit 114 projected by the light projector 112 and the light beam 124 from the interferometer 123 have different wavelengths. The selection of the wavelength can improve the signal, depending on the type of tissue. By way of example, short-wavelength light (<500 nm) is scattered particularly strongly by the cornea 211. Long-wavelength light (>1000 nm) is particularly suitable for penetrating the opaque tissue of the anterior chamber angle 23 as a result of its low scattering properties. By way of example, the wavelength of the projected light slit 114 has a wavelength of less than 500 nm and the light beam 124 from the interferometer 123 has a wavelength of more than 1000 nm, more particularly 1300 nm.

As illustrated schematically in FIGS. 4, 5, 6 and 7, the interferometric measurement system 12 emits a light beam 124 onto and into the eye 2 along the projection axis i and registers the light beam 125 along this projection axis i, which latter light beam was reflected in many layers, particularly along the tissue and material transitions between eye tissue and implants. The interference and hence delay is used by the interferometer 123 to carry out a punctiform axial distance measurement—and hence to determine the position—of geometric detailed structures that have different refractive indices in the eye by (A-scan). By successively moving the projection axis i—and hence the alignment of the projected and reflected light beams 124, 125—to a plurality of eye positions by means of the scanner 121, the interferometric distance measurement supplies distance values—and hence the form—of two- and three-dimensional geometric detailed structures in the eye 2. The interferometer 123 is able to not only determine the position of the boundary layers of geometric structures, but can also be extended to the effect of also visualizing birefringent structures, obtaining spectroscopic information and being able to visualize fluid flows within the tissue. As illustrated schematically in FIG. 2, determining the interferometric axial distance along suitably aligned projection axes i1, i2 allows the measurement of regions in the eye 2, for example the anterior chamber angle 215 in the anterior chamber region 21, or regions behind the iris 212 in the posterior chamber region 22, which cannot be visualized optically by the known triangulation methods. Depending on the embodiment variant, the scanner 121 is designed to move the projection axis i and/or the alignment of the projected and reflected light beams 124, 125 by deflecting a mirror and/or by means of a movement driver, the movement being effected by translational or rotational mechanical movement of the light projector used for projecting the light beam 124 from the interferometric measurement system 12.

The processing means 10 comprise one or more processors and program and data storage media, in which different programmed software modules for controlling the processor are stored. By way of example, the software modules comprise a triangulation module 101, an interferometry module 102, a positioning module 103 and a compilation module 104.

The triangulation module 101 is designed to determine the position and form of geometric references (e.g. the aforementioned two- and three-dimensional geometric (partial) structures) in the eye 2 from the diffuse reflections registered and stored by the camera 113 or from the cross-sectional parts of the eye 2 illuminated by the light slit 114 by using triangulation calculations within a defined reference measurement region.

The interferometry module 102 is designed to determine the form of geometric detailed structures in the eye 2 (B-scan, C-scan) within a defined detailed measurement region on the basis of a plurality of registered and stored axial interferometric distance measurements (A-scans) of the interferometer 123.

The positioning module 103 is designed to determine one or more defined geometric reference features of the eye 2, and to position the geometric detailed structures in the eye 2 on the basis of these geometric reference features. By way of example, the geometric reference features comprise the aforementioned structures, partial structures, inclusions, implants and/or (two-dimensional) shapes, speckles, markings or patterns that can be recognized thereon, which are determined (see FIG. 10) by the positioning module 103, for example by using image processing functions, firstly in the geometric references within the reference measurement region 3 determined by triangulation and secondly in the geometric detailed structures determined by interferometry within the detailed measurement region 4, and so the positioning of the detailed measurement region 3 in the reference measurement region 4 or the spatial position of the detailed structures in the eye 2 can be determined on the basis of the geometric reference features.

In one embodiment variant, the positioning module 103 is additionally designed to determine the expected beam profile of the light beam 124 from the interferometer 123 through the eye 2 on the basis of the position and form of the three-dimensional geometric structures in the eye 2 determined by the triangulating measurement system 11, more particularly on the basis of the boundary surfaces between tissue and material transitions of eye tissue and implants determined by these structures, and on the basis of refractive indices of the various eye tissue and implant regions, and to use this expected beam profile in addition to the positioning of the detailed measurement region 3 in the reference measurement region 4.

In a further embodiment variant, the positioning module 103 is moreover designed to accept instructions from the user, for example via a graphic/visual user interface, for determining and selecting one or more geometric target references in the eye (2) with respect to the determined, for example visualized, two-dimensional or three-dimensional geometric structures in the eye 2. The positioning module 103 then transmits the geometric target references, for example as coordinates or vectors, to the interferometric measurement system 12, which then aligns the projection axis i and hence the light beam 124 from the interferometer 123 onto this target reference for interferometric registration of the detailed measurement region 4. This function is particularly expedient for rediscovering pathologically changing tissue regions over relatively long periods of time.

Figure 10:
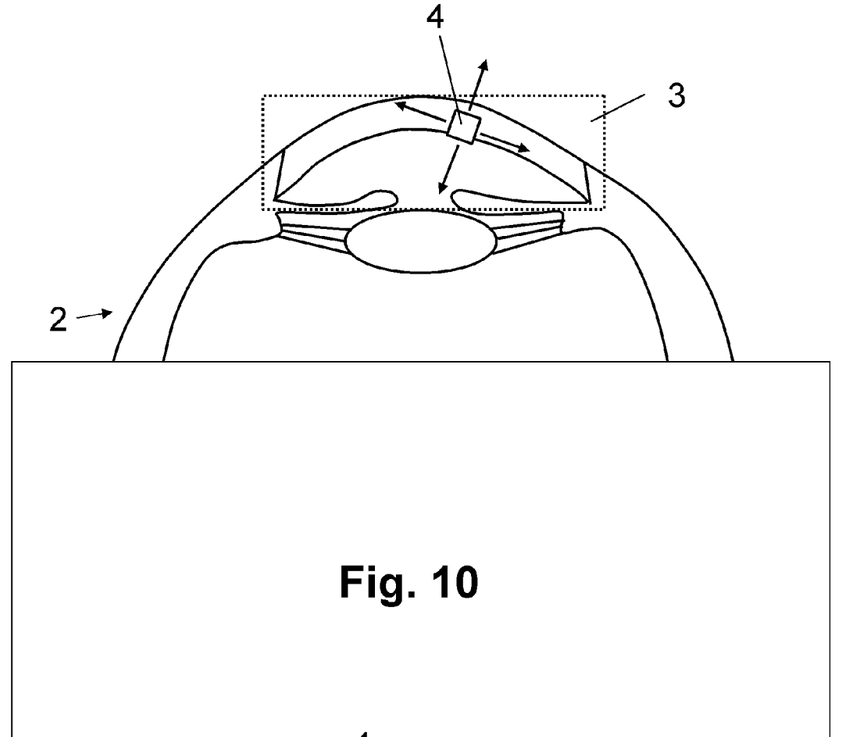
FIG. 10 shows a cross-sectional diagram that schematically illustrates a detailed measurement region of the interferometric measurement system, which region can move in the reference measurement region of the triangulating measurement system.
Figure 11:
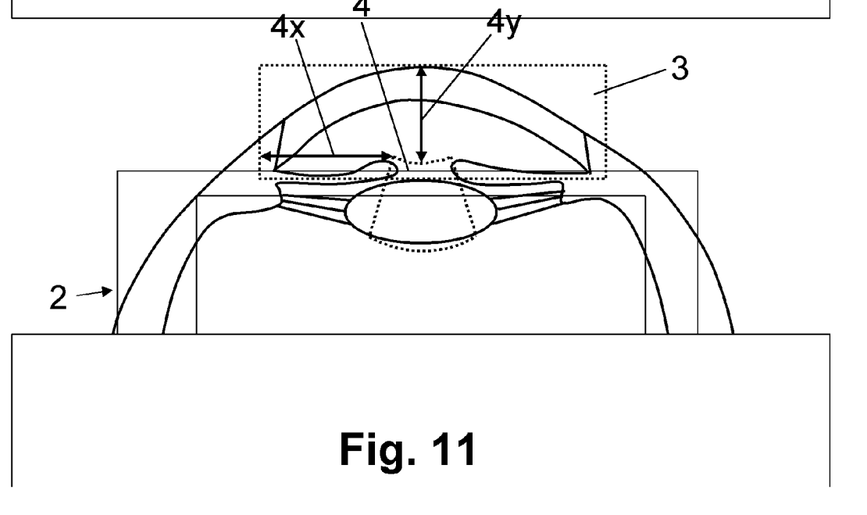
FIG. 11 shows a cross-sectional diagram that schematically illustrates a detailed measurement region of the interferometric measurement system, which region is fixed in the reference measurement region of the triangulating measurement system.

As illustrated schematically in FIGS. 10 and 11, the interferometric measurement system 12 is designed to determine the geometric detailed structures in a two- or three-dimensional detailed measurement region 4 of the eye 2, which detailed measurement region, compared to the two- or three-dimensional reference measurement region 3 measured by the triangulating measurement system 11, has significantly smaller dimensions and is arranged within the reference measurement region 3, overlaps the reference measurement region 3, adjoins the reference measurement region 3 or is arranged completely outside of the reference measurement region 3.

In the variant according to FIG. 10, the interferometric measurement system 12 or the projected light beam 124 thereof, and hence the detailed measurement region 4 with respect to the reference measurement region 3, can be displaced freely while the measurement with respect to the triangulating measurement system 11 is being carried out, and so the geometric detailed structures can be determined in a plurality of detailed measurement regions 4 and can be positioned with respect to the reference measurement region 3 via geometric reference features. Hence, this advantageously allows the realization of more compact and more cost-effective projection optical systems. Furthermore, it is therefore also possible for use to be made of interferometric (OCT) techniques that have a limited depth measurement range (e.g. frequency domain OCT) or should be operated at a high optical resolution.

In the variant according to FIG. 11, the interferometric measurement system 12 is mechanically fixed (coupled) with respect to the triangulating measurement system 11 by means of geometric settings 4$x$, 4$y$, which for example correspond to a geometric reference defined via a calibration body, before the measurement is carried out, and so the spatial position of the detailed measurement region 4, and hence the position of the geometric detailed structures, are fixedly defined with respect to the reference measurement region 3. The defined geometric reference, with respect to which the triangulating measurement system 11 and the interferometric measurement system 12 are set for calibration purposes, is, for example, the pupil 213, the front side 221 of the lens and/or the apex of the cornea 211, which are preferably represented by a calibration body or alternatively by a specific eye 2.

The compilation module 104 is designed to register and to store a plurality of geometric detailed structures positioned at various places in the eye 2, to position these geometric detailed structures or the associated detailed measurement regions 3 on the basis of the determined geometric references/reference features in the reference measurement region 3, and hence to position these with respect to one another, and to assemble these to a superordinate combined geometric detailed structure. Moreover, the compilation module 104 is designed to deform the individual geometric detailed structures after the positioning thereof in the reference measurement region 3 by stretching, compressing and/or distorting such that they fit as continuously as possible with the adjoining or overlapping transition regions thereof.

In the following sections, different embodiments of the measuring device 1 with different arrangements and combinations of the triangulating measurement system 11 and the interferometric measurement system 12 are described with reference to FIGS. 5, 6, 7, 8 and 9.

In the embodiment according to FIG. 5, the optical axis c of the camera 113 runs substantially along the optic axis of the eye 2 and the alignment of the projection axis p of the light projector 112 running at an angle to the optical axis c of the camera 113 is changed by the scanner 111 for scanning the eye 2 by means of a moveable deflection mirror. The projection axis i of the interferometric measurement system 12 is aligned obliquely to the optical axis c of the camera 113 and so regions that cannot be registered by triangulation, for example regions behind the iris 212, can be measured, as indicated schematically by the projection axis i1. By displacing and/or deflecting the projection axis i in the plane of the drawing and/or perpendicularly to the plane of the drawing, the scanner 121 allows interferometric measurement of the eye 2 over an extended detailed measurement region 4.

Figure 9:
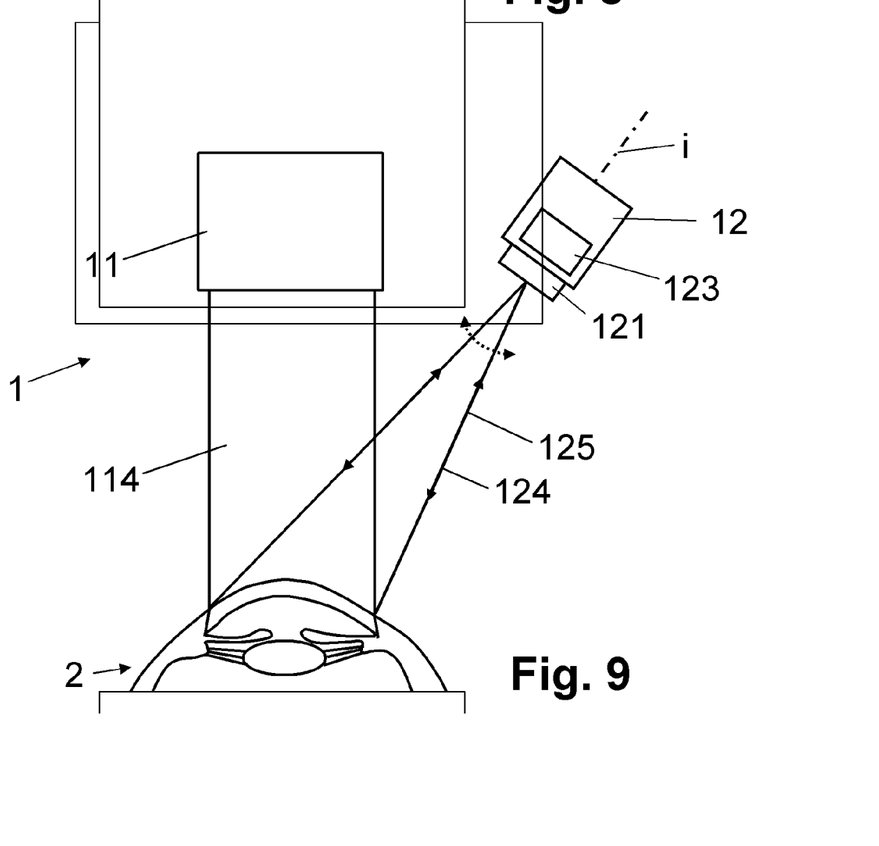
FIG. 9 shows a block diagram that schematically illustrates a further arrangement of the interferometric measurement system, in which the scan plane of the interferometric measurement system is situated in the plane of the light slit of the triangulating measurement system.

In the embodiment according to FIG. 6, the projection axis p of the light projector 112 runs substantially along the optic axis of the eye 2 and the optical axis c of the camera 113 is arranged obliquely with respect to the projection axis p of the light projector 112, and arranged in Scheimpflug configuration, i.e. the plane of the lens of the camera lens 1132 and the image registering plane of the imager 1131 intersect at a common point on the projection axis p of the light projector 112. The camera 113 and the light projector 112 are fix to one another mechanically and are rotated by a movement driver of the scanner 111 about a rotational axis d running through the projection axis p, which allows complete scanning of the eye 2 with the light beam or light slit 114. The projection axis i of the interferometric measurement system 12 is aligned obliquely to the projection axis p of the light projector 112, and so regions that cannot be registered by triangulation, for example regions behind the iris 212, can be measured, as indicated schematically by the projection axis i1. By displacing and/or deflecting the projection axis i in the plane of the drawing and/or perpendicularly to the plane of the drawing, the scanner 121 allows interferometric measurement of the eye 2 over an extended detailed measurement region 4. In a preferred variant, the interferometric measurement system 12, or at least the scanner 121, is mechanically fixed to the light projector 112 (and the camera 113) and is also rotated about the rotational axis d by the movement driver. In this variant, the scanner 121 is preferably designed such that the projection axis i, and hence the projected light beam 124, is deflected or moved in a scan plane that runs in the plane of the light slit 114, as illustrated in FIG. 9.

Figure 8:
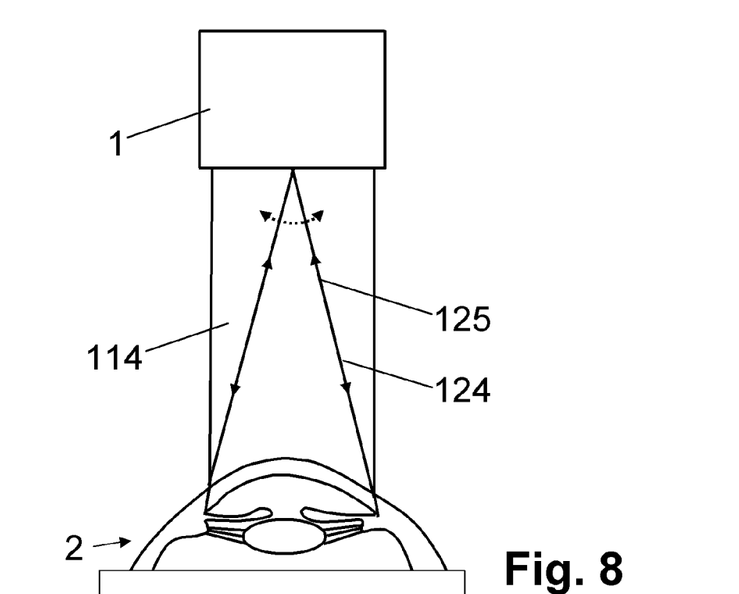
FIG. 8 shows a block diagram that schematically illustrates a scan plane of the interferometric measurement system, which plane is situated in the plane of the light slit of the triangulating measurement system.

In the embodiment according to FIG. 7, the projection axis p of the light projector 112 and the (central) projection axis i of the interferometric measurement system 12 run along a common axis, which for example runs along the optic axis of the eye 2. For this purpose, the projected light beam or light slit 114 of the light projector 112 and/or the projected light beam 124 from the interferometer 123 are mirrored onto this common axis by one or more deflection mirrors 110. In order to supply the reflected light beam 125 to the interferometer 123, the mirror 110 has a semitransparent design. As described in the context of FIG. 6, the camera 113 is arranged in Scheimpflug configuration with respect to the light projector 112 and is mechanically fixed to the light projector 112. The measuring device 1 optionally also has a second camera 113a arranged in Scheimpflug configuration, the camera lens 1132a and imager 1131a thereof being arranged mirror-symmetrical to the camera lens 1132 and to the imager 1131 with respect to the projection axis p of the light projector 112. The light projector 112 and the camera(s) 113, 113a and the interferometric measurement system 12, or at least the scanner 121 thereof, are rotated by the movement driver of the scanner 111 about a rotational axis d likewise running through the projection axis p. In this variant, the scanner 121 is preferably designed such that the projection axis i, and hence the projected light beam 124, is deflected or moved in a scan plane that runs in the plane of the light slit 114, as illustrated in FIG. 8.

In a combined variant of FIGS. 6 and 7, the interferometric measurement system 12 is designed such that the projection axis i thereof can firstly be brought into an alignment running obliquely to the projection axis p of the light projector 112 for interferometric measurements in regions that cannot be registered by triangulation, for example regions behind the iris 212, and secondly can be brought into an alignment coinciding with the projection axis p of the light projector 112 for triangulating and interferometric measurement regions that are as homogeneous as possible.

Although the present invention has been described in relation to particular embodiments thereof, many other variations and modifications and other uses will become apparent to those skilled in the art.

What is claimed is:

1. An ophthalmological measuring device for determining geometric structures of an eye, comprising an optical, triangulating first measurement system and an optical, interferometric second measurement system, wherein
   the first measurement system is configured to determine at least one geometric reference in the eye by triangulation,
   the second measurement system is configured to determine geometric detailed structures in the eye by optical interferometry, and
   the measuring device is configured to register and store the geometric detailed structures determined by the second measurement system, and to spatially position in the eye the geometric detailed structures, registered and stored by the measuring device, on the basis of the at least one geometric reference in the eye determined by the first measurement system.

2. The measuring device of claim 1, wherein the first measurement system and the second measurement system are mechanically coupled such that the geometric detailed structures in the eye are positioned on the basis of one or more geometric settings in a position of the first measurement system corresponding to the geometric reference.

3. The measuring device of claim 1, wherein the measuring device further comprises a positioning module designed to determine one or more geometric reference features of the eye and to position the geometric detailed structures on the basis of the geometric reference features in the eye.

4. The measuring device of claim 1, wherein the first measurement system comprises a light projector for projecting a light slit and a first scan module for moving the light slit to different positions of the eye, and wherein the second measurement system comprises an interferometer and a second scan module, with the second scan module being designed to project at least one light beam from the interferometer onto and into the eye at a plurality of different positions of the eye and to supply light reflected by the eye to the interferometer.

5. The measuring of claim 4, wherein the first scan module is configured to move the light slit along a scan direction, and wherein the second scan module is designed to move the light beam in a scan plane substantially parallel to or substantially normal to the scan direction.

6. The measuring of claim 4, wherein the first scan module is configured to move the light slit by rotation about a rotational axis substantially running in the light slit, and wherein the second scan module is designed to move the light beam in a scan plane, with a central projection axis of the second scan module forming an angle with the rotational axis or running along the rotational axis.

7. The measuring device of claim 5, wherein the first scan module and the second scan module are configured and coupled such that the light slit and the scan plane are situated in a common plane.

8. The measuring device of claim 6, wherein the first scan module and the second scan module are configured and coupled such that the light slit and the scan plane are situated in a common plane.

9. The measuring device of claim 4, wherein the light slit projected by the light projector and the light beam from the interferometer have different wavelengths.

10. The measuring device of claim 4, wherein the first measurement system comprises at least one camera arranged in Scheimpflug configuration for registering cross-sectional parts of the eye illuminated by the light slit.

11. The measuring device of claim 1, wherein the measuring device comprises a compilation module configured to register a plurality of geometric detailed structures positioned differently in the eye, to position these geometric detailed structures with respect to one another on the basis of the at least one geometric reference and to assemble said structures to form a superordinate combined geometric detailed structure.

12. The measuring of claim 11, wherein the compilation module is designed to deform suitably the geometric detailed structures for assembling the superordinate combined geometric detailed structure.

13. The measuring device of claim 1, wherein the first measurement system is configured to determine the geometric reference in a defined reference measurement region of the eye, wherein the second measurement system is configured to determine the geometric detailed structures in a detailed measurement region of the eye, which detailed measurement region is significantly smaller than the defined reference measurement region, and wherein the measuring device comprises movement drivers for moving the second measurement system for determining geometric detailed structures in a plurality of different detailed measurement regions of the eye.

14. The measuring device of claim 13, wherein the detailed measurement region of the eye is arranged with respect to the defined reference measurement region as per at least one of the following options: within the defined reference measurement region, overlapping with the defined reference measurement region, adjoining the defined reference measurement region and outside of the defined reference measurement region.

15. The measuring device of claim 1, wherein the first measurement system and the second measurement system have a common light source.

16. The measuring device of claim 4, wherein the wavelength of the projected light slit is less than 500 nm and the wavelength of the light beam from the interferometer is more than 1000 nm.

17. The measuring device of claim 16, wherein the wavelength of the light beam from the interferometer is 1300 nm.

18. An ophthalmological measurement method for determining geometric structures of an eye, comprising:
  determining at least one geometric reference in the eye by an optical, triangulating first measurement system,
  determining geometric detailed structures in the eye by an optical interferometric second measurement system,
  registering and storing the geometric detailed structures in the eye determined by the second measurement system, and
  spatially positioning in the eye the geometric detailed structures, registered and stored, on the basis of the at least one geometric reference determined by the first measurement system.

\* \* \* \* \*